US007777010B2

(12) United States Patent
Logtenberg

(10) Patent No.: US 7,777,010 B2
(45) Date of Patent: Aug. 17, 2010

(54) USE OF A NATIVE EPITOPE FOR SELECTING EVOLVED BINDING MEMBERS FROM A LIBRARY OF MUTANTS OF A PROTEIN CAPABLE OF BINDING TO SAID EPITOPE

(75) Inventor: Ton Logtenberg, Werkhoven (NL)

(73) Assignee: Crucell Holland B.V., Leiden (NL)

(*) Notice: Subject to any disclaimer, the term of this patent is extended or adjusted under 35 U.S.C. 154(b) by 912 days.

(21) Appl. No.: 10/186,186

(22) Filed: Jun. 28, 2002

(65) Prior Publication Data

US 2003/0096226 A1 May 22, 2003

Related U.S. Application Data

(60) Division of application No. 10/184,508, filed on Jun. 27, 2002, which is a continuation of application No. PCT/NL00/00941, filed on Dec. 21, 2000.

(30) Foreign Application Priority Data

Dec. 27, 1999 (EP) .................................. 99204561

(51) Int. Cl.
*C12P 21/08* (2006.01)
*C07K 5/00* (2006.01)
(52) U.S. Cl. .............................. 530/388.85; 530/388.8; 530/388.15; 530/388.1; 530/387.9; 530/387.1; 530/380; 530/327; 530/329
(58) Field of Classification Search .............. 530/388.2, 530/387.7, 387.3, 387.1, 388.85, 388.8, 388.15, 530/388.9, 380, 329, 327; 435/DIG. 3
See application file for complete search history.

(56) References Cited

U.S. PATENT DOCUMENTS

| 5,811,238 | A | 9/1998 | Stemmer et al. |
| 6,265,150 | B1 | 7/2001 | Terstappen et al. |
| 6,787,638 | B1* | 9/2004 | Watkins et al. ......... 530/388.85 |

OTHER PUBLICATIONS

Luiten et al, Human Antibodies, 1997, 8(4) 169-180.*
Balzar et al, J. Mol. Med. 91997) 77, 699-721.*
Velders et al, Jrnl. of Immunotherapy, (1996), 19(4),245-256.*
PCT International Search Report, PCT/NL00/00941, dated Jul. 9, 2001, 3 pages.
PCT International Preliminary Examination Report, PCT/NL00/00941, dated Dec. 14, 2001, 8 pages.
Abdullah et al., The role of monocytes and natural killer cells in mediating antibody-dependent lysis of colorectal tumour cells, Cancer Immunol. Immunother, 1999, pp. 517-524, vol. 48.
Partial European Search Report, EP 1 273 918 A3, dated Mar. 5, 2003, 4 pages.
Hoogenboom et al., Selection-dominant and nonaccessible epitopes on cell-surface receptors revealed by cell-panning with a large phage antibody library, Eur. J. Biochem, 1999, pp. 774-784, vol. 260.

Huls et al., A recombinant, fully human monoclonal antibody with antitumor activity constructed from phage-displayed antibody fragments, Nature Biotechnology, Mar. 1999, pp. 276-281, vol. 17.
Huls et al., Antitumor Immune Effector Mechanisms Recruited by Phage Display-derived Fully Human IgG1 and IgA1 Monoclonal Antibodies, Cancer Research, Nov. 15, 1999, pp. 5778-5784, vol. 59.
Lekkerkerker et al., Phage antibodies against human dendritic cell subpopulations obtained by flow cytometry-based selection on freshly isolated cells, Journal of Immunological Methods, 1999, pp. 53-63, vol. 231.
Vaughan et al., Human antibodies by design, Nature Biotechnology, Jun. 1998, pp. 535-539, vol. 16.
Davis et al., Ligand Recognition by$\alpha\beta$T Cell Receptors, Annu. Rev. Immunol., 1998, pp. 523-544, vol. 16.
Xu et al., Diversity in the CDR3 Region of $V_H$ is Sufficient for Most Antibody Specificities, Immunity, 2000, pp. 37-45, vol. 13, Cell Press.
Altschul, Stephen F., et al., "Gapped BLAST and PSI-BLAST: a new generation of protein database search programs," 25(17) Nucleic Acids Research 3389-3402 (1997).
Balint, Robert F., et al., "Antibody engineering by parsimonious mutagenesis," 137 Gene 109-118 (1993).
Balzar, Maarten, et al., "Cytoplasmic Tail Regulates the Intercellular Adhesion Function of the Epithelial Cell Adhesion Molecule," 18(8) Molecular and Cellular Biology 4833-4843 (Aug. 1998).
Barbas, III, Carlos F., et al., "In vitro evolution of a neutralizing human antibody to human immunodeficiency virus type 1 to enhance affinity and broaden strain cross-reactivity," 91 Proc. Natl. Acad. Sci. USA 3809-3813 (Apr. 1994).
Berek, Claudia, et al., "Mutation Drift and Repertoire Shift in the Maturation of the Immune Response," 96 Immunol. Rev. 23-41 (1987).
Burton, Dennis R., et al., "Human Antibodies from Combinatorial Libraries," 57 Advances in Immunology 191-280 (1994).
Clackson, Tim, et al., "Making antibody fragments using phage display libraries," 352 Nature 624-628 (Aug. 1991).
Chowdhury, Partha S., et al., "Improving antibody affinity by mimicking somatic hypermutation in vitro," 17 Nature Biotechnology 568-572 (Jun. 1999).
Dykxhoorn, Derek M., et al., "Killing the Messenger: Short RNAs that Silence Gene Expression," 4 Molecular Cell Biology 457-467 (Jun. 2003).
Ghetie, Maria-Ana, et al., "Homodimerization of tumor-reactive monoclonal antibodies markedly increases their ability to induce growth arrest or apoptosis of tumor cells," 94 Proc. Natl. Acad. Sci. USA 7509-7514 (Jul. 1997).
Hawkins, Robert E., et al., "Selection of Phage Antibodies by Binding Affinity Mimicking Affinity Maturation," 226 J. Mol. Biol. 889-896 (1992).
Hoogenboom, Hennie R., "Designing and optimizing library selection strategies for generating high-affinity antibodies," 15 Tibtech 62-70 (Feb. 1997).

(Continued)

*Primary Examiner*—T. D. Wessendorf
(74) *Attorney, Agent, or Firm*—TraskBritt

(57) ABSTRACT

The invention provides a method for selecting at least one member from a library of proteinaceous molecules by providing at least one cell and/or a functional equivalent thereof, with at least part of the library under conditions that allow binding of any such member to an epitope in and/or on the cells and/or the functional equivalent thereof, removing unbound proteinaceous molecules and selecting the at least one member, wherein the library includes at least one mutant of a proteinaceous molecule capable of binding to the epitope.

20 Claims, 5 Drawing Sheets

OTHER PUBLICATIONS

Hoogenboom, Hennie R., et al, "Selection-dominant and nonaccessible epitopes on cell-surface receptors revealed by cell-planning with a large phage antibody library," 260 Eur. J. Biochem. 774-784 (1999).

Huls, Gerwin A., et al., "A recombinant, fully human monoclonal antibody with antitumor activity constructed from phage-displayed antibody fragments," 17 Nature Biotechnology 276-281 (Mar. 1999).

de Kruif, John, et al., "Selection and Application of Human Single Chain Fv Antibody Fragments from a Semi-synthetic Phage Antibody Display Library with Designed CDR3 Regions," 248 J. Mol. Biol. 97-105 (1995).

Kwong, Peter D., et al., "Structure of an HIV gp120 envelope glycoprotein in complex with the CD4 receptor and a meutralizing human antibody," 393 Nature 648-659 (Jun. 1998).

Lekkerkerker, Annemarie, et al., "Phage antibodies against human dendritic cell subpopulations obtained by flow cytometry-based selection on freshly isolated cells," 231 Journal of Immunological Methods 53-63 (1999).

Low, Nigel M., et al., "Mimicking Somatic Hypermutation: Affinity Maturation of Antibodies Displayed on Bacteriophage Using a Bacterial Mutator Strain," 260 J. Mol. Biol. 359-368 (1996).

McKeithan, Timothy W., "Kinetic proofreading in T-cell receptor signal transaction," 92 Proc. Natl. Acad. Sci. USA 5042-5046 (May 1995).

Pei, Xue Y., et al., "The 2.0Å resolution crystal structure of a trimeric antibody fragment with noncognate $V_H$-$V_L$ domain pairs shows a rearrangement of $V_H$ CDR3," 94 Proc. Natl. Acad. Sci. USA 9637-9642 (Sep. 1997).

Schier, Robert, et al., "Isolation of High-affinity Monomeric Human Anti-c-erbB-2 Single chain Fv using Affinity-driven Selection," 255 J. Mol. Biol. 28-43 (1996).

Stemmer, Willem P.C., "DNA shuffling by random fragmentation and reassembly: In vitro recombination for molecular evolution," 91 Proc. Natl. Acad. Sci. USA 10747-10751 (Oct. 1994).

Torigoe, Chikako, et al., "An Unusual Mechanism for Ligand Antagonism," 281 Science 568-571 (Jul. 1998).

Torigoe, Chikako, et al., "Shuttling of initiating kinase between discrete aggregates of the high affinity receptor for IgE regulates the cellular response," 94 Proc. Natl. Acad. Sci. USA 1372-1377 (Feb. 1997).

Tutt, Alison L., et al., "Monoclonal Antibody Therapy of B Cell Lymphoma: Signaling Activity on Tumor Cells Appears More Important Than Recruitment of Effectors," 161 The Journal of Immunology 3176-3185 (1998).

Vaughn, Tristan J., et al., "Human antibodies by design," 16 Nature Biotechnology 535-539 (Jun. 1998).

Wedemayer, Gary J., et al., "Structural Insights into the Evolution of an Antibody Combining Site," 276 Science 1665-1669 (Jun. 1997).

Winter, Greg, et al., "Making Antibodies by Phage Display Technology," 12 Annu. Rev. Immunol. 433-455 (1994).

Winter, Greg, et al., "Man-made Antibodies," 349 Nature 293-299 (Jan. 1991).

Yang, Wei-Ping, et al., "CDR Walking Mutagenesis for the Affinity Maturation of a Potent Human Anti-HIV-1 Antibody into the Picomolar Range," 254 J. Mol. Biol. 392-403 (1995).

Blazar et al., J. Mol. Med., 1996, pp. 699-712, vol. 77.

Co-pending U.S. Appl. No. 09/940,386 (abandoned), filed Aug. 27, 2001, Logtenberg et al., Title: Differentially Expressed Epitopes and Uses Thereof.

Co-pending U.S. Appl. No. 09/909,244 (abandoned), filed Jul. 19, 2001, Logtenberg et al., Title: A Selectively-Expressed Epitope on the Human CD38 Molecule Detected by a Phage Display Library-Derived Human SCFV Antibody Fragment.

Co-pending U.S. Appl. No. 10/184,508 (on appeal), filed Jun. 27, 2002, Ton Logtenberg, Title: Use of a Native Epitope for Selecting Evolved Binding Members From a Library of Mutants of a Protein Capable of Binding to Said Epitope.

* cited by examiner

```
          FR1                    CDR1           FR2                    CDR2         FR3                                        CDR3           FR4
UBS-54  QVQLVQSGAEVKKPGSSVRVSCKAS GGTFSSY AISWVRQAPGQGLEWMGGI IPIFGT ANYAQKFQGRVTITADESTSTAYMELSSLRSEDTAVYYCAR DPFLHY WGQGTLVT
A37     ------------------------- ------- ------------------- ------ ---------------------------------------- ------ --------
C52     -------A--K-------------- ------- ------------------- V----- ---------------------------------------- ------ --------

FR1                    CDR1              FR2                  CDR2        FR3                                    CDR3                FR4
UBS-54  EIELTQSPLSLPVTPGEPASISC RSSQSLLHSNGYNYLD WYLQKPGQSPQLLIY LGSNRAS GVPDRFSGSGSGTDFTLKISRVEAEDVGVYYC MQALQT FTF GPGTKVEI
A37     ----------------------- -A--TISN         ---A---Q--R--A-R---- AA-S--T -I------T--------L--P--FA---- A-GELYPRQF -G---L--
C52     -----GTLSLS---R-TL----- ----SV-S         S---------P---------- G------- -------------S--------------- ---------D-
```

Fig. 2

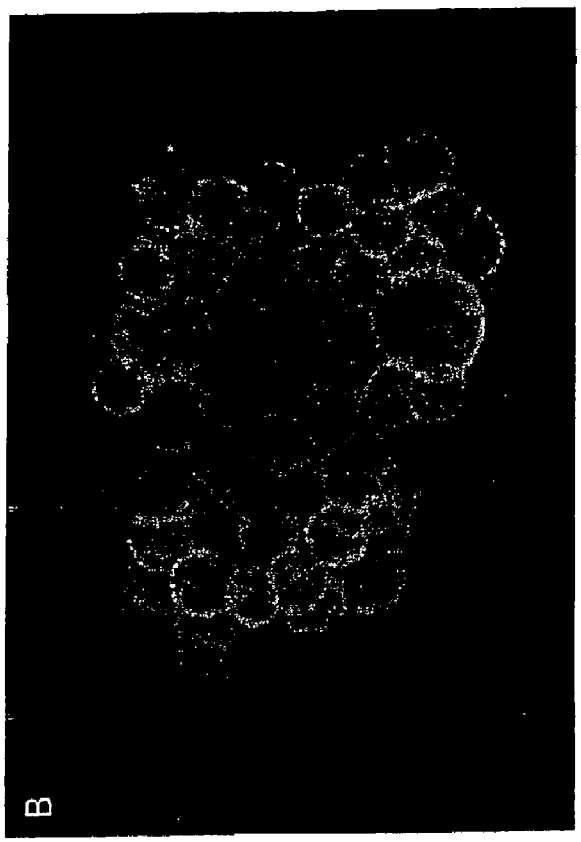
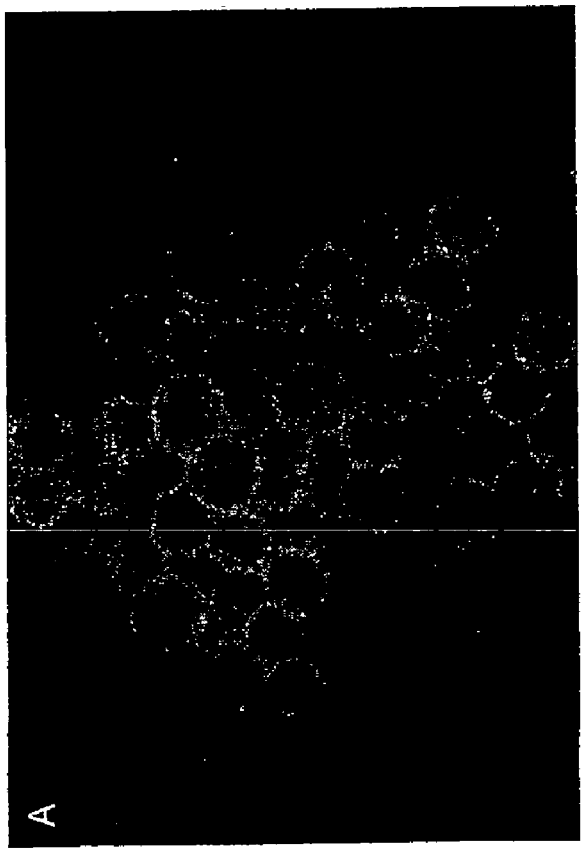
Fig. 5

USE OF A NATIVE EPITOPE FOR SELECTING EVOLVED BINDING MEMBERS FROM A LIBRARY OF MUTANTS OF A PROTEIN CAPABLE OF BINDING TO SAID EPITOPE

CROSS-REFERENCE TO RELATED APPLICATION

This application is a divisional of U.S. application Ser. No. 10/184,508, filed Jun. 27, 2002, which is a continuation of International Application Number PCT/NL00/00941 filed on Dec. 21, 2000, designating the United States of America, International Publication No. WO 01/48485 (Jul. 5, 2001), the contents of the entirety of which is incorporated by this reference.

BACKGROUND OF THE INVENTION

The invention relates to the field of biotechnology. More in particular the invention relates to the field of antibodies and uses thereof. One of such uses relates to medical uses of antibodies.

The exposure to a highly diverse and continuously changing environment requires a dynamic immune system that is able to rapidly adapt in order to adequately respond to potentially harmful micro-organisms. Higher organisms have evolved specialized molecular mechanisms to ensure the implementation of clonally-distributed, highly diverse repertoires of antigen-receptor molecules expressed by cells of the immune system: immunoglobulin (Ig) molecules on B lymphocytes and T cell receptors on T lymphocytes. For B lymphocytes, a primary repertoire of (generally low affinity) Ig receptors is established during B cell differentiation in the bone marrow as a result of rearrangement of germline-encoded gene segments. Further refinement of Ig receptor specificity and affinity takes place in peripheral lymphoid organs where antigen-stimulated B lymphocytes activate a somatic hypermutation machinery that specifically targets the immunoglobulin variable (V) regions. During this process, B cell clones with mutant Ig receptors of higher affinity for the inciting antigen are stimulated into clonal proliferation and maturation into antibody-secreting plasma cells (reviewed in 1).

In recent years, recombinant DNA technology has been used to mimic many aspects of the processes that govern the generation and selection of natural human antibody repertoires (reviewed in 2,3). The construction of large repertoires of antibody fragments expressed on the surface of filamentous phage particles and the selection of phages by panning on antigens has been developed as a versatile and rapid method to obtain antibodies of desired specificities (reviewed in 4,5). Further optimization of the affinity of individual phage antibodies has been achieved by creating mutant antibody repertoires that are expressed on bacteriophage particles and sampled for higher affinity mutants by selection for binding to antigen under stringent conditions (reviewed in 6). Various approaches have been used to create mutated antibody repertoires, including chain shuffling (7, 8), error prone PCR (9), use of E. coli mutator strains (10) or approaches more specifically directed to the complementarity determining regions (CDRs) of the antibody molecule, like CDR walking and parsimonious mutagenesis (11-13).

To select higher affinity mutants from a library of phage-displayed, mutagenized antibody fragments, selections have been performed on purified immobilized antigen or biotinylated antigen in solution, followed by capture of phage bound on streptavidin magnetic beads (14-16). It has been demonstrated that the selection of higher affinity single chain Fv antibody fragments (scFv) specific for the antigen c-erb-2 from phage libraries of mutants of that scFv was dependent on the availability of purified antigen in solution. Antigen captured on a solid phase resulted in the isolation of false positives with higher avidity rather than affinity due to the dimerization and oligomerization of the scFv on the phage. In addition, it was shown to be crucial for the isolation of higher affinity scFv to perform subsequent rounds of phage selections with carefully controlled and increasingly lower antigen concentrations in solution (14). Although very high-affinity scFv have been isolated with these approaches, they are not readily applicable when the target antigen is difficult to express as a recombinant molecule or tedious to purify in sufficient quantities without losing its native configuration. Examples of these types of molecules are seven-transmembrane spanning proteins, insoluble lipid-modified membrane molecules and post-translationally-modified proteinaceous molecules that are specific for particular cell types or disease states. Thus a selection procedure for higher affinity mutant antibody fragments, without the need for purified antigen would represent an important extension of affinity maturation strategies for phage displayed antibodies.

The invention now in one aspect provides a method for selecting a member from a library of proteinaceous molecules comprising providing cells and/or a functional equivalent thereof, with at least part of said library under conditions that allow binding of any member to an epitope in and/or on said cells and/or said functional equivalent thereof, removing unbound proteinaceous molecules and selecting said member, wherein said library comprises at least one mutant of a proteinaceous molecule capable of binding to said epitope. Preferably a mutant comprises one or more mutations that affect the capability of binding of the mutant to said epitope in a positive or negative way, compared with the unmutated proteinaceous molecule. The capability may be affected by an altered binding affinity or altered dissociation constant, or both.

A member of the library is a proteinaceous molecule present in said library and/or a proteinaceous molecule selected from said library. A selected member typically comprises the capacity to bind to said epitope. Once selected and characterized a member may also be generated in another way for instance artificially, through molecular biological techniques such as but not limited to peptide synthesis or the expression of a nucleic acid encoding said proteinaceous molecule. A proteinaceous molecule may be a peptide, a polypeptide or a protein. Peptides are strings of amino acids linked together by a peptide bond. Although not precisely defined, peptides typically comprise between 2 and 50 amino acids. Polypeptides are longer peptides that may contain up to thousands of peptide bond-linked amino acids. The words polypeptide and protein are often interchangeably used to describe single, long polypeptide chains. In addition, proteins may consist of multiple polypeptide chains that collectively form the basis of a complex three-dimensional structure. A peptide, a polypeptide and/or a protein may comprise modifications such as those generated by a cellular protein modification machinery. A mutant of a proteinaceous molecule is a proteinaceous molecule comprising one or more changes compared to the unmutated proteinaceous molecule. A change can comprise for instance an exchange, a deletion, an insertion or an addition of one or more amino acids or a combination of these changes. Preferably but not necessarily said mutation is generated through a change in a nucleic acid encoding said proteinaceous molecule.

A library comprises at least one mutant of a proteinaceous molecule capable of binding to an epitope. Typically, a library will comprise more than 100 different mutants of said proteinaceous molecule. Such a library may be used on its own or it may be combined with one or more other libraries comprising at least one mutant of another proteinaceous molecule capable of binding to at least a part of said epitope. An advantage of such a combination is that it increases the complexity of mutants thereby increasing the odds for finding a particularly favorable mutant. A library may of course also be combined with other libraries or proteinaceous molecules. One such combination may be occasioned by the desire to provide a library comprising an array of mutants of different proteinaceous molecules capable of binding to different epitopes present on a certain target molecule.

An epitope according to the invention is typically present in and/or on a protein produced by a cell. An epitope is a binding site capable of binding said proteinaceous molecule. An epitope may be (part of) any kind of molecule. Typically, an epitope comprises a peptide, a polypeptide, a protein and/or a modification produced by a cellular protein modification machinery.

The cells to which at least part of the library is provided can be living cells and/or dead cells. Typically cells are obtained from a culture. Cells may be processed prior to providing at least part of the library. For instance, for fixation purposes and/or permeabilisation purposes. A functional equivalent of cells is a crude cellular extract. In such an extract the structure of the cells is usually distorted in such a way that individual cells can essentially not be recognised through microscopic means. A crude extract may have undergone several steps to remove one or more undesired components. However, extracts comprising essentially only a proteinaceous molecule comprising said epitope are not considered crude extracts. The division line between what can be considered to be a crude extract and what must be considered to be a purified extract is difficult to give. However, extracts comprising more or less intact organelles are functionally equivalent to cells. A functional equivalent of a cell must comprise most of the epitope in a form essentially similar to a form the epitope has when it is present in and/or on an intact cell comprising said epitope.

Removal of the part of the library that is not bound to the cells and/or the functional equivalent thereof, can be achieved through washing the cells and/or functional equivalent thereof with a suitable solution such as a buffered isotonic solution. Cells can be washed easily by pelleting the cells and suspending the cells in a suitable solution. For removal of that part of the library that is not bound to a functional equivalent of cells, such as an extract of cells, it is advantageous to attach the functional equivalent thereof to a carrier thus enabling easy manipulation of the functional equivalent. Cells may of course also be attached to a carrier. A preferred method of removing unbound proteinaceous molecules is by means of one or more washing steps. It is advantageous to provide for one or more stringent washing steps to remove proteinaceous molecules that are bound with an eventually undesired low affinity. For cells or parts thereof such as organelles and/or membranous particles attachment to a carrier is not required, though may still be advantageous. A method of the invention usually comprises more than 10,000 cells or functional equivalent thereof. However, lower amounts of cells or equivalent thereof may also be used. The invention can even be performed using only one cell.

A proteinaceous molecule may be any proteinaceous molecule capable of binding to an epitope. Non-limiting examples of such a proteinaceous molecule are an antibody (artificial or natural), a FAB-fragment (artificial or natural), a single chain Fv fragment, a T-cell receptor, a ligand, a receptor, a peptide selected preferably from a library for specific epitope binding capacity or a matrix attachment protein. Of course, functional equivalents of said proteinaceous molecules may also be used. Such a functional equivalent comprises the same epitope binding activity in kind not necessarily in amount. A functional equivalent may be a part, a derivative and/or an analogue of said proteinaceous molecule. A derivative is typically obtained through amino acid substitution. A proteinaceous molecule is said to be able to bind to an epitope when cells comprising said epitope, upon exposure to said proteinaceous molecule followed by one or more washing steps, are found to retain said proteinaceous molecule to a significantly higher extend than other cells, essentially not comprising said epitope.

In a preferred embodiment of the invention said proteinaceous molecule comprises a single chain Fv fragment (scFv) and/or a FAB fragment, or a functional equivalent thereof. A functional equivalent of said scFv and/or said FAB fragment is a part, derivative and/or analogue of said scFv and/or said FAB comprising essentially the same binding activity as said scFv and/or FAB fragment in kind not necessarily in amount.

In a preferred embodiment each of said mutants of a proteinaceous molecule is physically linked to a vehicle comprising nucleic acid encoding said mutant proteinaceous molecule. This has the advantage that when said member is recovered from said cells and/or functional equivalent thereof, one simultaneously recovers nucleic acid encoding said proteinaceous molecule. Said nucleic acid is then available for multiplication, analysis, subcloning and/or expression in a cell.

Preferably, said vehicle comprises a virus-like particle such as a phage capsid or a functional equivalent thereof. A virus-like particle is preferred since it is able to condense nucleic acid into a manageable form. A virus-like particle is also preferred for the reason that it may be used to efficiently introduce the nucleic acid of the selected member into a cell. This is particularly advantageous when the nucleic acid, once introduced in the cell, is capable of multiplication, thus allowing for instance the easy isolation of relatively large amounts of said nucleic acid.

In another preferred aspect of the invention said epitope comprises a tumour-associated epitope. A tumour-associated epitope is an epitope essentially characteristic for tumour cells in a body. Said epitope can be present in other cells as long as it is not present in said other cells in the same way as in tumour cells. For instance, an epitope is a tumour-associated epitope when it is present on the surface of a tumour cell and essentially not present on the surface of non-tumour cells due to, for instance but not limited to, a substantially lower expression of said epitope in non-tumour cells. Said epitope may also be present on other cells as long as said cells do not normally co-exist with tumour cells in the same body. A typical example is a tumour-associated epitope present on foetal cells but essentially not present on normal adult cells. A tumour-associated epitope may be individually determined, i.e. a tumour-associated epitope for one individual may not be a tumour-associated epitope in another individual of the same species. A tumour-associated epitope may also be a part of a protein that is present on normal cells but wherein the glycosylation of the protein in normal cells is different from the glycosylation of the protein on tumour cells.

In another aspect the invention provides a molecule capable of binding to said epitope, comprising at least part of a member obtained with a method according to the invention.

In one embodiment said part comprises a part of the epitope binding site of said member, or a functional equivalent thereof. In another embodiment said part is a part not directly involved in epitope binding. One example of such a part not directly involved in epitope binding is a part involved in the association with complement factors. Another example is a part associated with tissue penetration of said proteinaceous molecule. This may be due to altered epitope binding properties or due to other mutations. A part can of course comprise more than one property. For instance a part may comprise the epitope binding site and a part involved in association with complement factors. Preferably said molecule comprises an antibody or a functional part thereof. Said antibody is preferably synthesised artificially. Preferably, in a cell cultured in vitro. In one embodiment said antibody is human, humanised and/or human-like, or a functional equivalent thereof.

In another aspect the invention provides the use of a cell and/or a functional equivalent thereof displaying an epitope for obtaining an evolved epitope binding molecule with an enhanced property as compared to the epitope binding molecule said evolved epitope binding molecule is at least in part derived from. In one embodiment said epitope binding molecule comprises a part of a complementarity determining region of an antibody or a functional equivalent thereof. In another embodiment said property comprises an enhanced epitope binding property. In yet another embodiment said property comprises an enhanced tissue penetration property and/or an enhanced complement activation property.

In one embodiment of the invention higher affinity huMabs that bind to the tumor-associated antigen Ep-CAM were obtained by constructing small phage display libraries of mutant scFv antibody fragments derived from the parental anti-Ep-Cam scFv UBS-54. These libraries were subsequently panned on intact Ep-Cam-positive tumor cells. Stringent washing steps during phage selections resulted in the isolation of scFv C52, which was converted into an intact IgGl huMab with a 15-fold affinity improvement and a KD=4*$10^{-10}$ M. The affinity improvement resulted mainly from a lower $k_{off}$ (or dissociation constant). Light chain shuffling and DNA shuffling were employed to introduce mutations in the antibody V regions. The approximately four fold increase in affinity achieved with each of these mutagenesis approaches were comparable to results achieved by antibody affinity maturation using other mutagenesis and phage display selection techniques (11, 14, 33). In the present invention it is demonstrated that affinity selection can be performed on intact fixed cells, precluding the need to purify or express the target antigen as a recombinant molecule.

Previous selection procedures for isolation of higher affinity antibody variants from phage display libraries have used purified soluble antigen or antigen immobilized on a solid phase as targets for phage selections. It has been noted that selection on solid-phase-bound antigen results in the preferential selection of dimeric over monomeric scFv, due to avidity, thus interfering with the selection of truly higher affinity scFv (14). Selection in solution reduces the avidity effect but requires the careful and step-wise reduction of target antigen concentration in subsequent selection rounds (14). As has been noted for other scFv, in solution scFv UES-54 is a mixture of dimers (30%) and monomers (70%). This ratio was maintained in mutants A37, B43, and C52, showing that the selection on intact cells did not result in a biased selection for dimers (data not shown) Screening for higher affinity binders out of a selected phage pool has been carried out by ranking of mutant scFv according to a lower $k_{off}$ as determined by surface plasmon resonance (6). Although it was attempted to rank the selected scFv according to this method, it was found the experimental data with crude periplasmic scFv preparations was difficult to evaluate due to complexity of the affinity plots (RU versus time) resulting from the mixtures of monomers, dimers and aggregates. Therefore, it was decided to pursue clones that were dominating the phage pools after three rounds of selection. Of note, dominance of phage clones in selections is not entirely determined by affinity but also influenced by scFv expression level, folding efficiency and level of toxicity to *E. Coli*. Although in the analysis, the presence of dominant clones correlated with higher affinity scFv, it cannot be excluded that other, higher affinity yet less dominant clones were present in the selected phage pools.

Light chain shuffling resulted in the replacement of the original Vk2 light chain by a Vk3 light chain in mutant A37. Structural analysis revealed that the canonical structure of the Vk3 light chain in A37 consisted of a much shorter loop, creating a broader interaction surface. Thermodynamically, it is attractive for antigen-antibody interactions to have a large and close interaction surface because more water molecules are excluded (gain in solvent entropy) and, more importantly, many simultaneous interactions (hydrogen bonds, van der Waals and dipole-dipole interactions) can occur between epitope and paratope (contributing to binding enthalpy) (23). Structurally, this results in a broad face binding site of the antibody that is complementary to an equally broad epitope on a large interacting protein. In contrast, binding sites consisting of deep clefts that snugly surround antigen are generally associated with small ligands such as peptides and low molecular weight organic molecules (23).

DNA shuffling of the VL region but not the VH region resulted in the isolation of higher affinity antibodies. The modeled structure of high affinity huMab C52 indicated that only one of the seven mutations within the VL region, $Asn^{L30A}$→Ser, most likely directly affects the interaction with Ep-CAM. The other mutations can result in more subtle optimization of the antibody binding site through additional hydrogen bonds and improved packing interactions, as previously reported (21), rather than a specific improved interaction between one of the mutated antibody residues and the antigen Ep-Cam. Indeed, mutation $Ser^{L31}$ results in an additional hydrogen bond with $Val^{L29}$ that stabilizes the LCDR1 loop. The major gain in affinity appears to be caused by mutations located at the periphery of the antigen combining site in CDR1, resembling the distribution of mutations found in in vivo somatically mutated V regions (34).

Antibody-mediated killing of solid tumors in vivo is a complex process involving Fc receptor-bearing effector cells of the immune system, complement factors and signaling events resulting from the interaction between the antibody and its target. The relative importance and contribution to this process by antibody-related characteristics such as affinity and isotype are becoming the focus of antibody research, spurred by the recent successes of engineered antibodies in the clinic. We exploited the engineered high and lower affinity anti-Ep-CAM huMabs to study two aspects of antibody affinity-dependent processes: killing of tumor cells and penetration of antibodies into clusters of tumor cells mimicking micrometastasis.

It was then found that the lower affinity UBS-54 penetrated faster into the center of the multicell spheroid, resulting in a homogeneous distribution of the huMab. This observation supports other studies showing that very high affinities of antibodies (>$10^9$ $M^{-1}$) lead to trapping of antibody at the tumor edge and slow their penetration into the tumor interior (31, 32, 35, 36).

To our surprise, the lower affinity huMab UBS-54 mediated a persistently higher specific tumor cell lysis with PBMC as effector source compared to the higher affinity mutant C52. The same results were obtained with target cells transfected with an Ep-CAM cDNA construct lacking a cytoplasmic tail, suggesting that signaling via Ep-CAM did not play a role in tumor cell killing. Although many FcγR are able to trigger ADCC, the high affinity FcγRI appears to be the most effective trigger molecule (37,38). We propose that quantitative differences in activation of effector cells mediated via binding of antibodies to high affinity FcγRI may affect their killing capacity in ADCC. Although the mechanism has not been elucidated for FcγRI, recent experiments with the FcεR, another high affinity member the multichain immune recognition receptor family, have shown that aggregation of this receptor by an excess of low-affinity ligand leads to the sequestration of the receptor associated kinase Lyn (39). As a consequence, a smaller number of aggregates simultaneously induced by a higher affinity ligand become deprived of Lyn and are thus unable to initiate the signaling cascade (38). In this model, scarcity of a receptor associated kinase prevents low affinity interactions to activate the complete signaling cascade (40, 41). Based on our in vitro tumor cell killing data we hypothesize that extensive FcγRI receptor triggering by very high affinity antibodies may also result in sequestration of receptor associated kinases and consequently result in a less-efficient FcγRI-mediated induction of the cascade of events leading to activation of effector cells.

The CDCC experiments showed a significantly higher specific tumor cell lysis with huMab C52 compared to huMab UBS-54, indicating an advantage of higher affinity antibodies in activating the complement system. Although the improved capacity of the higher affinity mutant in activating the complement system is evident in vitro, several studies indicate that CDCC may play a marginal role in in vivo tumor cell killing. Most tumor cells express complement-inhibiting regulators which protect the cells against lysis by autologous complement (42-46). Furthermore, tumor cell-specific monoclonal antibodies have been found to be equally effective in eradicating tumors in mice deficient in complement factor C5 as in control mice (47). Thus, ADCC may be the dominant immunological mechanism to kill tumor cells, suggesting that the lower affinity UBS-54 with its higher killing capacity in ADCC may be favorable for passive immunotherapy.

EXAMPLES

Materials and Methods

Mutagenesis an Affinity Maturation:

The scFv UBS-54, isolated from a semisynthetic phage antibody display library, is encoded by members of the VH1 and Vk2 heavy and light chain variable region gene families (17,48). For light chain shuffling, total RNA was isolated from peripheral B blood cells of a pool of 15 donors, converted to cDNA by oligo(dT) priming and amplified by PCR using Vk2 gene family specific primers with Nco-I and Xho-I restriction sites: Vk2-NCO-I (5'-'GCCTCCACCTCCATGG-GATATTGTGATGACTCAGTCT-3') (SEQ ID NO: 1) and Vk2-XHO-I (5'GCCTCCACCTCTCGAGCTGCTGACAG-TAATAAGTTGCAAAATC-3') (SEQ ID NO: 2). Amplified 35 products were purified, digested with appropriate restriction enzymes, cloned into vector pPV containing the original UBS54 heavy chain, transformed into XL-1blue bacteria and plated on ampicillin containing 2TY plates as described (48). The resulting shuffled library contained $2*10^7$ individual clones.

For phage selections, LS174T colon carcinoma cells were washed in PBS and fixed in 1% paraformaldehyde for 15 min at 4° C. For selection of higher affinity mutants, $10^6$ fixed cells and the shuffled library were incubated for 2 hours at 4° C. and the cells were washed 3 times in 50 ml ice cold medium. The stringent washing procedure consisted of incubation of fixed cells in 1% BSA/PBS containing 0, 5% tween 80 at 37° C. Every 15 minutes, cells were washed and transferred to a new eppendorf tube, this procedure was repeated 16 times. Finally, cells were washed twice in PBS, and phages were eluted by resuspending the final cell pellet in 500 μl 100mM HCL for 5 minutes, followed by neutralization with 250 μl M Tris/HCl pH7.4. Phages were propagated and 2 additional rounds of selection were performed using the same procedure except that the number of washing cycles increased with 3 in every subsequent round. After the last round of selection, 70 colonies were randomly picked and used for nucleotide sequence analysis.

DNA shuffling of the VH gene was performed, according to a procedure described in detail elsewhere (18,19). In brief, cDNA from peripheral blood B cells was amplified using primers specific for the VH1 gene family :NCO-I- V-H1: 5'GCCTCCACCTCCATGGCCCAGGTG-CAGCTGGTGCAGTCTGG3' (SEQ ID NO: 3) and pan VH XHO-I : 5'GCCTCCACCTCTCGAGTCTCGCACAG-TAATACACGGCCG3' (SEQ ID NO: 4).

After purification, 2 μg of PCR product was treated with DNA'se I (Sigma, St.Louis, Mo.) to generate DNA fragments ranging in size between 50 and 100 base pairs. These fragments were reassembled in a volume of 100 μl with 800 μl M dNTP's, 0.2 units of Taq polymerase (Supertaq, HT biotechnology Ltd. Cambridge, UK) in the manufacturer's recommended buffer in the absence of primers. Reassembly PCR consisted of 40 cycles of 30 s at 94° C., 30 s at 50° C. and two min at 72° C. The reassembled PCR product was used in a 1/30 dilution in a subsequent PCR (20 cycles) with the primer NCOVH1 and a spiked primer XHO-HCDR3-UBS-54:5' GCCTCCACCTCTCGAGACGGTGACCAGGG TACCT-TGGCCCCA[ATA(CAT/AGG/ACC)][GTG(AAA/CTT/GGC)][AAG(CTA/AGT/ACC)][AAA(CTT/AGG/ACC)] [CGG(AAA/CTT/CCC)][GTA(AAT/CGG/GCC)]T CTTGCACAGTAATACACGGCCGTGTC3' (SEQ ID NO: 5). The nucleotides between circular brackets comprise 10% of the mixture. Spiked oligo primer of HCDR3 introduced an average replacement of 2 of the 6 amino acids in the original HCDR3 of UBS-54. PCR product was digested with Ncol and Xhol and cloned in pPV vector containing the A37 light chain. This resulted in a library of $4*10^7$ clones. The library was incubated with fixed LS174T cells at room temperature for 2 hours and subjected to the stringent washing procedure. After 3 rounds of selection the nucleotide sequence of 64 clones was analyzed.

For DNA shuffling of the light chain, the following primers were used: NCO Vk2 and Vk2-XHO. After DNA'se I treatment and reassembly PCR the reassembled product was amplified using the same primers, digested with Sacl and Not 1 and cloned in the pPV vector containing the VH gene of clone B43. Except increased number of washing cycles, phage selections with this library of $1*10^7$ clones were identical to those descibed above. After 3 rounds of selection, 70 clones were picked for nucleotide sequence analysis, resulting in the identification of a single dominant clone (31/70 clones) named clone C52.

Construction and Evaluation of Intact huMabs

The VH and VL regions encoding scFv A37, B43 and C52 were excised and recloned into expression vectors for the synthesis of complete human IgGl/K molecules as described in detail elsewhere (17, 49). In a two step cloning procedure, the VH and VL regions encoding the scFvs were first inserted into the vector pLEADER to append the T-cell receptor α-chain HAVT leader peptide sequence and a splice donor site. In the second cloning step, the VH or VL regions, which contain leader and splice donor sites, were subcloned in the pNUT-Cγl or pNUT-Ck expression vectors using appropriate restriction sites. Subsequently, the constructs were stably transfected in BHK cells. In brief, cells were maintained at 37° C. in a 5% $CO_2$ humidified incubator in Iscove's modified Dulbeccos medium containing 10% FCS, 2 mM glutamine and 10 µg/l gentamicine (complete medium). Cells were transfected at a density of 70-80% confluency using calcium phosphate-plasmid DNA precipitation for 4 h at 37° C., followed by a 15% glycerol shock for 1 min. Selection was initiated by adding 80 µM methotrexate (Sigma, St. Louis, Mo.). After 2 weeks, colonies of resistant cells were picked and cultured in methotrexate-containing medium. Production of huMabs was determined in the supernatant by quantitative ELISA. Integrity of protein-A purified recombinant huMabs was determined by SDS/PAGE and by Coomassie brilliant blue staining of gels. Concentration of purified huMab was determined by spectrophotometry at 280 nm. For immunofluorescence staining, 10 µl of purified huMab IgGl at a concentration of 10 µl/ml was used. HuMabs were detected by FITC conjugated goat anti-human IgG (Southern Biotechnology Associates, Birmingham, Ala.). The L929 fibroblast cell line and L929 cells transfected with human Ep-CAM cDNA (LME-6) were a kind gift of Dr. S. Litvinov (University of Leiden, The Netherlands) (50).

Affinity Measurements

In separate BIAcore flow cells, approximately 160, 1565 and 4154 resonance units of purified recombinant Ep-CAM produced in insect cells (kindly provided by Dr. D. Herlyn, Wistar institute, Philadelphia, Pa.) (25 µg/ml) in 10 mM acetate buffer (pH 4.0) were coupled to a CM5 sensor chip using NHS/EDC coupling chemistry. Association and dissociation were measured under continuous flow of 30 ml/min using a concentration range from 100 to 1 nM.

Structural Analysis

After initial sequential and structural alignment using the automatic classification described by Martin and Thornton (51), structure 1GC1 (52), deposited with the Protein Data Bank (53), was chosen as scaffold for the heavy chain of all models. To create a scaffold for the non-canonical CDR H3, a loopsearch was performed with the program SYBYL v.6.5 (Tripos Inc., St. Louis, Mo., USA) between residues $Gly^{94}$ and $phe^{100y}$ of 1GC1. These positions, deviating relatively little in torsion angles (26), precede a more variable part of the CDR H3. In addition, regions 92-94 and 100y-104 show high sequential similarity with 1GC1. Structure 1NQB (54) with the CDR L3 loop of 1JRH (55) was used as scaffold for the light chain of antibody UBS-54. Structure 1FIG (56) was used as scaffold for the light chains of models A37 and C52. Actual modeling was performed with the BLDPIR module of WHAT IF v.19970813-1517 (57). The quality was checked with PROCHECK v.3.3 (58) and the WHATCHECK module of WHAT IF. A knowledge base was created by analysis of the following antigen-antibody complexes, selected from the Protein Data Bank: 1BAF, 1CBV, 2GCR, 1CLZ, 1DBB, 1EAP, 1FIG, 1FLR, 1GAF, 1HYX, 1IBG, 1IGJ, 1IND, 1KEL, 1KNO, 2MCP, 1MFA, 1MRD, 1MPA (hapten class), 1ACY, 1TET, 1FPT, 1FRG, 1GGI, 2IGF (peptide class), 1AFV, 1DVF, 1FBI, 1VFB, 3HFL, 3HFM, 1LAI, 1IKF, 1JEL, 1JHL, 1MLC, 1NCD, 1NMB, 1OSP (protein class). The programs used for analysis are: HBPLUS (59) "AS INTEGRATED IN LIGPLOT" v. 3.0 (60), NACCESS v. 2.1.1 (Hubbard, S. J., and Thornton, J. M. 1993. "NACCES", Computer Program, Department of Biochemistry and Molecular Biology, University College London), DISCOVER v. 97.0 (Molecular Simulations Inc., San Diego, Calif., USA) and SYBYL. Protein sequence analysis was carried out with the program BLAST v. 2.0 (61).

Antibody and Complement-Dependent Cellular Cytotoxicity

The cytolytic activity of human peripheral blood polymorphonuclear cells (PMN) and mononuclear cells (PBMC) was evaluated in a standard $^{51}Cr$ release assay (62). Briefly, target tumor cells were labeled with 150 µCi of $^{51}Cr$ (Amersham, Buckinghamshire, UK) for 2 h at 37° C. After extensive washing, target cells were plated in U-bottom microtiter plates at a concentration of $5*10^3$ cells/well. Isolated human PMN and PBMC were added to each well at an effector:target ratio of 80:1. Cells were incubated at 37° C. in the presence of various concentrations of purified antibodies in a final volume of 200 µl. For whole blood ADCC assays, 50 µl/well of heparinized peripheral blood was added as a source of effector cells. Complement-mediated lysis was performed with 50 µl of serum. After 4 h, $^{51}Cr$ release was determined in triplicate. The percentage of cellular cytotoxicity was calculated according to the formula: % specific lysis=([experimental cpm-basal cpm]/[maximal cpm-basal cpm])*100%, with maximal $^{51}Cr$ release determined after lysing target cells with 10% Zapoglobin (Coulter, Pittsburgh, Pa.), and basal release measured after incubating target cells with medium alone. Heparinized peripheral blood was collected from healthy volunteers. PMN and PBMC were isolated by Ficoll-Histopaque discontinuous gradient centrifugation, as previously described (63). Contaminating erythrocytes were removed by hypotonic shock with 0.2% NaCl. Effector cells were more than 95% pure, as determined by cytospin preparations and more than 95 viable as assessed by trypan blue exclusion. For ADCC and CDCC experiments, LS174T tumor cells and HCA cells transfected with human Ep-CAM (HCE) or with cytoplasmic tail-deleted human Ep-CAM (HCM), both under transcriptional control of a metallothionine promoter, were used as target cells (64). HCE and HCM cells were kindly provided by Dr. S. Litvinov (Dept. of Pathology, University of Leiden, The Netherlands).

Antibody Penetration in Multicell Spheroids

Purified antibodies UBS-54 and mutant C52 were labelled with FITC according to standard procedures. Naturally-occurring multicell spheroids of the Ep-CAM+GLC-8 carcinoma cell line were incubated for various times with FITC labelled huMabs and analyzed using a Bio-Rad MRC-1000 CLSM (BioRad, Hercules, Calif.). The confocal images were recorded after 10-15 minutes of incubation at the center of the multicell spheroid as described (65).

Results

Generation and Selection of Mutant Libraries

Recently, we have described the isolation of a scFv directed against the tumor-associated Ep-CAM molecule and its conversion into an intact, functional human IgG1 antibody with an affinity of 5 nM (19). The germline Vk2 light chain of this antibody was replaced by Vk light chains obtained by PCR amplification of cDNA extracted from pooled blood lymphocytes of 15 healthy individuals. A phage display library of $2 \times 10^7$ clones was generated and subsequently panned on paraformaldehyde fixed Ep-Cam+LS174T colon carcinoma cells. of note, 24 randomly picked clones from the unselected library all bound to the Ep-CAM transfected LME-6 cell line but not the parental L929 cell line in flow cytometric analysis, showing the dominant role of the VH gene in determining the Ep-CAM specificity. The cells with bound phages were incubated at 37° C. and washed every 15 minutes with PBS/tween (0.5%) for 16 cycles. In preliminary experiments, it was determined that phages expressing the UBS-54 scFv could not be detected in flowcytometry on LS174 colon carcinoma cells after these stringent washing procedures. Approximately $10^7$ phages could be recovered after the first, second and third round of selection, while the number of washing cycles increased with 3 for each subsequent round. Nucleotide sequence analysis of randomly picked clones from the third round of selection revealed an identical Vk sequence in approximately 50% of the clones. This clone was named A37.

Crystallographic and CDR grafting studies have convincingly shown that both mutations in the CDR and framework regions of V regions may contribute to affinity improvement of antibodies (20,21). We therefore selected DNA shuffling as a second mutagenesis strategy because it results in the introduction of mutations in both CDR and framework regions. DNA shuffling introduces point mutations and exchange of stretches of DNA between homologous genes, thereby mimicking natural protein evolution (18,19). In addition, this mutation strategy potentially introduces CDR blocks that already have been selected for favorable amino acids like Tyr, Trp, Ser, and Asp. The amino acids Tyr, Trp, Ser, and Asp are favorable for antigen binding because they have a low conformational degree of freedom (less entropy to loose) and they participate in a variety of molecular interactions such as hydrogen bonds, van der Waals interactions, dipole-dipole interactions, and aromatic p-stacking (Tyr and Trp) (22,23). The VH1 gene encoding scFv UBS-54 was mixed with amplified VH1 gene segments from the pool of healthy donors. Fragments of 50-100 base pairs obtained after DNA'se I digestion were used in a reassembly PCR, and subsequently amplified with a VH1-specific 5' primer and a 'spiked' CDR3 primer. The spiked oligonucleotide primer was designed to introduce a low rate of mutations in the CDR3 region of the VH1 gene segments. A small library of $4*10^7$ VH1 mutagenized clones was constructed by ligating PCR-amplified material in the construct containing the A37 light chain. This library was subsequently selected on intact fixed cells. Sequence analysis of 24 clones randomly picked from the unselected DNA shuffled library demonstrated an average of approximately 18 mutations in the entire VH gene with an average of 2.6 mutations in the CDR3 region. This number of mutations dropped to approximately 4 mutations in each VH gene after three rounds of selection. Of note, all clones analyzed after three rounds of selection contained the original UBS-54 CDR3 region. Because no single dominant clone could be detected after three rounds of selection for binding to LST174 carcinoma cells, clone B43 was randomly chosen for further analysis. This choice was based on the observation that it contained a number of mutations frequently observed in other clones in this collection. Subsequently DNA shuffling with the light chain was performed using the collection of Vk gene segments used for the construction of the light chain shuffled library. The resulting library comprised $1*10^7$ clones and was selected for binding to the intact cells under stringent conditions. After three rounds of selection, sequence analysis was performed and revealed a single dominant clone (31 out of 70 sequences), named clone C52.

Reconstruction of Intact huMabs

The V regions of mutant scFv A37, B43 and C52 were recloned in eukaryotic expression vectors for the production of IgG1 huMabs in BHK cells (17). Immunoglobulin was purified from the supernatant of stably-transfected cell lines using protein A affinity chromatography as described (17) Although intact and functional huMabs could be isolated from the supernatant of clone B43 (data not shown), it did not reveal significant improvement of affinity for recombinant Ep-CAM in BiaCore analysis (see next paragraph). Therefore, the original UBS-54 and the A37 and C52 mutants were focused on. The integrity of the IgG1/K huMabs A37 and C52 was confirmed by Coomassie staining of SDS/PAGE gels run under denaturing and non-denaturing conditions (FIG. 1). Purified huMabs A37 and C52 retained their specificity as determined by binding to the Ep-CAM transfected LME-6 cell line but not the non-transfected L929 parental cell line (FIG. 1).

Biacore Analysis

The kinetic association and dissociation rates of the original huMab UBS-54 and the mutant huMabs A37 and C52 were determined by surface plasmon resonance (Table 1). The original huMab UBS-54 and the murine anti-Ep-CAM antibody 323/A3 were used as controls, revealing an average KD of 6 nm and 0,5 nM respectively. HuMab A37 with the shuffled Vk light chain demonstrated an affinity of 1,6 nM (~4 told increase). The binding affinity of the huMab C52 containing the DNA-shuffled Vk light chain was improved 15 fold compared to the original UBS-54 huMab, yielding a huMab with a KD=4 $*10^{-10}$ nM. The improvement was mainly the result of a lower dissociation constant.

Structural Analysis

Sequence analysis shows that the light chain selected in mutant A37 displays only 54% sequence homology with the original light chain in UBS-54 and possesses a shorter CDR1 sequence (FIG. 2). The A37 light chain is a member of the Vk3 gene family with the highest degree of homology to DPK22/A27 germline gene segment (24). Although the Vk primer preferentially anneals to Vk2 genes, it was noted that Vk3 genes are also present in the shuffled library. The shorter CDR1 loop in C52 appears to protrude to a lesser extent in the antigen binding site, creating a flat contact interface that is energetically favorable in anti-protein antibodies (23; FIG. 3).

The affinity matured mutant C52 differs from A37 by three amino acid changes in the heavy chain (the mutations of VH B43, introduced by DNA shuffling of VH) and by eight additional mutations in the light chain (the mutations of VL C52, introduced by DNA shuffling of VL) (FIG. 2 and FIG. 3). Mutations $Ser^{H16} \rightarrow Ala$, $Arg^{H19} \rightarrow Lys$, $Arg^{L40} \rightarrow Pro$, $Ser^{L65} \rightarrow Thr$ and $Glu^{L105} \rightarrow Asp$ are located within the framework, far away from the combining site and are likely not involved in stabilization of the conformation of the CDR loops. Mutation $Ile^{H52} \rightarrow Val$ in CDR H2 can result in removal of a repulsive steric interaction of the Cd atom of $Ile^{H52}$. However, because mutant B43 with the same mutations shows no significant increase in antigen binding affinity (data not shown), the overall effect of this mutation appears to be small. Residue L50 (mutation $Ala^{L50} \rightarrow Gly$) is frequently involved in antigen contact according to the knowledge base. A change in the backbone conformation of CDR L2, due to the higher conformational freedom of Gly is not likely, as CDR L2 has a conserved canonical structure (25). Presumably because of the relatively large distance between the top of CDR L2 and the surface of the antibody, which includes the antigen binding site, the high energy interactions appear to be reserved for amino acids with large side chains.

Four mutations are located in the CDR L1, $Thr^{L28} \to Ser$, $Ile^{L29} \to Val$, $Asn^{L30} \to Ser$ and $Asn^{L31} \to Ser$ (FIG. 2 and FIG. 3). The knowledge base reveals that antibody positions L28, L29 and L31 very rarely interact in protein-antibody complexes, in contrast to position L30A. In case of position L28 (mutation $Thr^{L28} \to Ser$), this is probably due to its peripheral location. The side chain of A37 $Ile^{L29}$ is buried within the CDR L1, stabilizing the loop through packing interactions, which are mimicked by C52 $Val^{L29}$. The side chain of A37 $Asn^{L31}$ appears to be turned away from the binding site. Mutation C52 $Ser^{L31}$ allows an additional hydrogen bond between its hydroxyl group and the main chain carbonyl group of $Val^{L29}$, further stabilizing the CDR L1 loop. Hotspot mutation $Asn^{L30A} \to Ser$ is most likely to affect the interaction with Ep-CAM directly.

Functional Analysis

The availability of two anti-tumor huMabs with the same epitope specificity but different affinities allowed us to precisely assess the influence of affinity on in vitro tumor cell killing capacity in antibody and complement dependent cellular cytotoxicity assays (ADCC and CDCC respectively). ADCC with LS174T tumor target cells and PBMC as a source of effector cells consistently resulted in 10% lower tumor cell lysis with the high-affinity huMab C52 compared to the original huMab UBS54 (FIG. 4). The persistently lower tumor cell lysis mediated via huMab C52 occurs with saturating antibody concentrations, indicated by the plateau shape in the curve (FIG. 4). Based on animal studies and the improved performance of chimeric human/mouse monoclonal antibodies in patients, ADCC is considered to be an important immunological mechanism in tumor cell killing (26, 28). A direct inhibitory effect of therapeutic antibodies on tumor cell growth or induction of tumor cell apoptosis, mediated via binding of antibodies to their target receptor may also contribute to clinical efficacy (29, 30). To assess whether the less efficient tumor cell lysis mediated via C52 is independent of signal transduction via Ep-Cam, ADCC was performed with HMA cell lines transfected with full-length Ep-CAM cDNA or with a mutant Ep-CAM cDNA lacking the cytoplasmic tail. With both transfectants, the same less efficient tumor cell killing of the high-affinity mutant huMab C52 was reproducibly observed, suggesting that the observed difference in killing capacity between UBS54 and C52 is not influenced by variations in signal transduction via Ep-CAM (data not shown).

The same experiments performed with whole blood instead of purified PBMC as a source of effector cells demonstrated a significantly more efficient tumor cell lysis with the high-affinity mutant huMab C52 (FIG. 4). It was hypothesized that the improved performance of the high-affinity huMab C52was caused by a more efficient CDCC. Indeed, huMab C52 more efficiently mediated tumor cell killing in the absence of effector cells and with serum as a source of complement (FIG. 4). Apparently, the lower dissociation rare of mutant huMab C52 results in a more efficient crosslinking of complement fragment Clq.

Influence of Antibody Affinity on Penetration in Multicell Speroids of Tumor Cells Deep percolation and uniform distribution through the tumor of monoclonal antibodies applied in immunotherapy of solid tumors is considered to be important for optimal therapeutic effect. In vitro and in vivo studies have suggested that transport of antibodies through the tumor interstitium is retarded by its specific binding to the tumor antigen. This so-called binding site barrier is a function of binding affinity, antigen concentration, and the antibody transport coefficients (31, 32). To determine the relative binding site barrier effect of the high and lower affinity anti-tumor huMabs, an in vitro multicell spheroid model system was employed. The small cell lung carcinoma cell line Glc-8, that expresses high levels of Ep-CAM and grows in multicell spheroids of about 100 cells, was incubated with 10 mg of FITC-conjugated UBS-54 or C52. Confocal laser scanning microscopy of the spheroids after 10-15 minutes of incubation unveiled a binding site barrier with the higher affinity huMab. At this timepoint, uniform binding of huMab UBS-54 to cells in the spheroids was observed, whereas binding of the higher affinity mutant C52 was almost restricted to the outer cell layer (FIG. 5). After one hour of incubation, uniform binding to all cells in the spheroids was observed for both antibodies (data not shown).

BRIEF DESCRIPTION OF THE DRAWINGS

FIG. 2: Sequence comparison of the original UBS-54 (SEQ ID NO: 14) and the higher affinity mutants A37 (SEQ ID NO: 15) and C52 (SEQ ID NO: 16). Note the shorter CDR1 sequence in the shuffled Vk3 light chain. Numbering is according to Chothia (25).

FIG. 5: Confocal scanning laser microscope images recorded within the center of Glc-8 multicell spheroids with FITC labeled huMab UBS-54 (A) and FITC labeled huMab C52 (B).

TABLE 1

Figure 1:
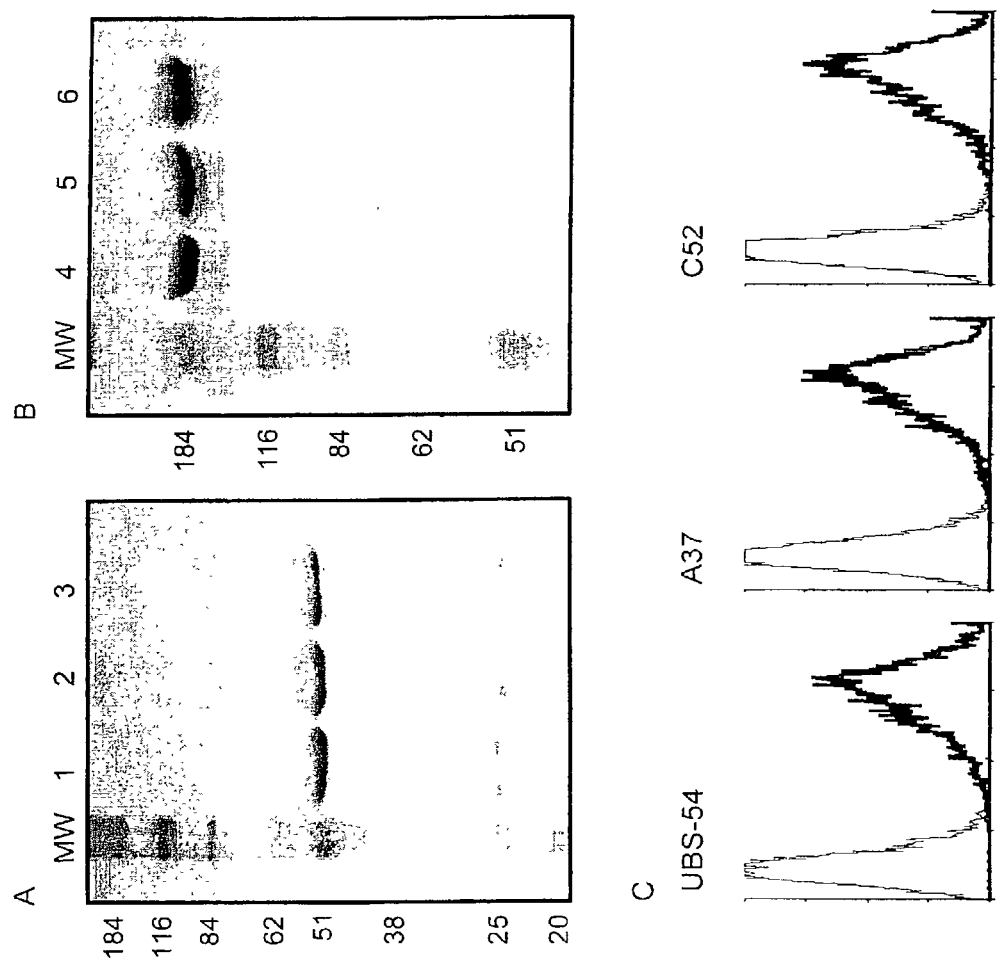
FIG. 1: SDS/PAGE analysis of purified huMabs under reducing (A) and non-reducing (B) conditions (UBS-54, lane 1 and 4; A37, lane 2 and 5; C52, lane 3 and 6). MW: molecular weight markers in kilodaltons. Panel C: staining of the Ep-CAM-negative parental L929 cell line (thin line) and stably transfected Ep-CAM-positive cells (bold line) with huMab UBS-54, huMab A37, and huMab C52.
Figure 3:
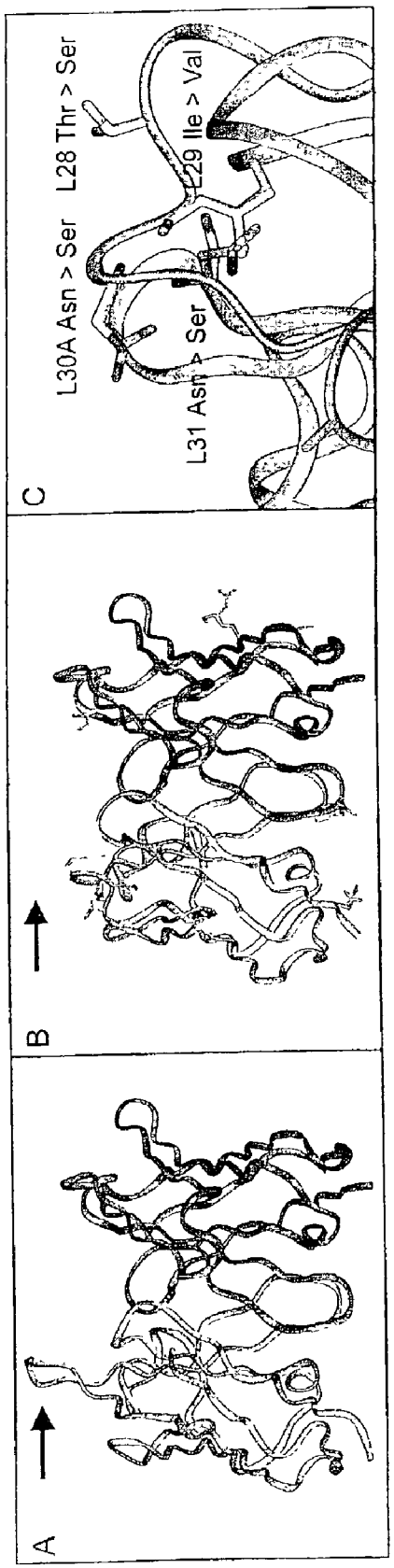
FIG. 3: Modelling of the original UBS-54(A) and the mutagenized antibody V regions of C52 (B) shows the shorter canonical structure of LCDR1 (arrow). The magnification (C) shows the positions of the mutated residues in LCDR1 ($Thr^{L28} \to Ser$, $Ile^{L29} \to Val$, $Asn^{L30A} \to Ser$ and $Asn^{L31} \to Ser$). Position $SerL^{30}$ most likely directly affects the interaction with Ep-CAM. A hydrogen bond beween $Ser^{L31}$ and $Val^{L29}$ results in stabilisation of the LCDR1 loop.
Figure 4:
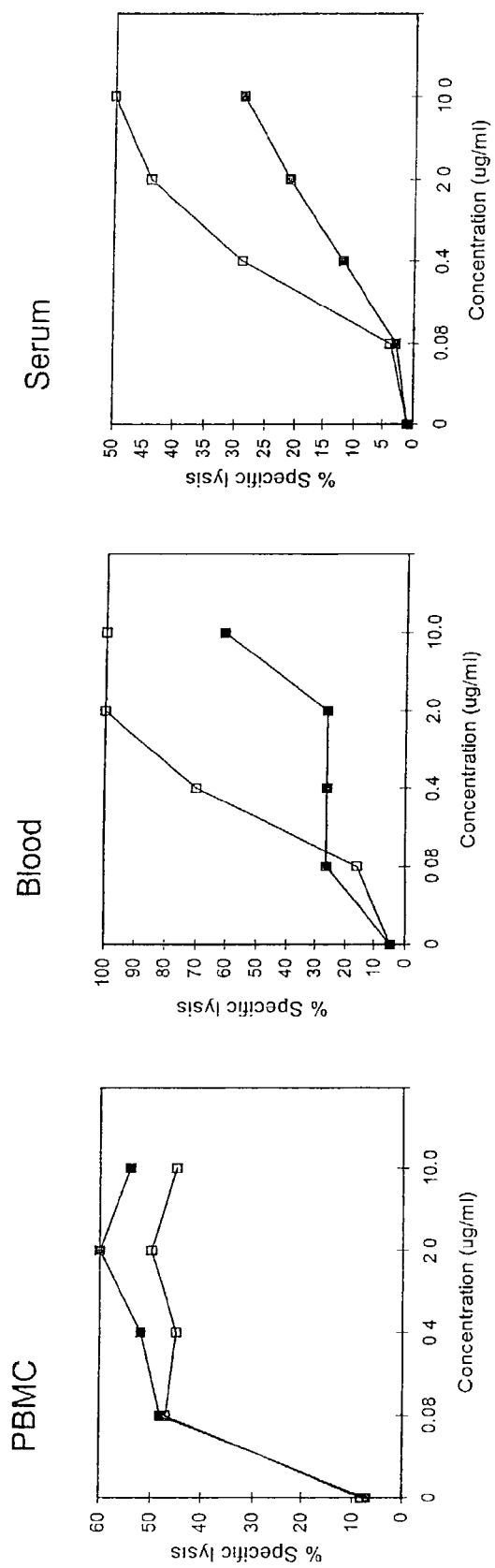
FIG. 4: Antibody-dependent cellular cytotoxicity (ADCC) and complement-dependent cellular cytotoxicity (CDCC) using huMab UBS-54 (■) and huMab C52 (▨). The shown experiments are representative for at least 6 experiments performed with effector cells of different donors.

Affinities and binding kinetics of huMabs UBS-54, A37, and C52. Standard error of the mean is indicated between brackets.

| IgG1 | Ka(1/Ms) * $10^5$ | Kd(1/s) * $10^{-4}$ | KD(nM) |
|---|---|---|---|
| UBS-54 | 1.0(0.3) | 6.0(0.7) | 6.0 |
| A37 | 2.5(0.3) | 4.1(0.4) | 1.6 |
| C52 | 2.7(0.6) | 1.1(0.8) | 0.4 |

REFERENCES

1. Berek, C., & Milstein, C. 1987. Mutation drift and repertoire shift in the maturation of the immune response. *Immunol. Rev.* 96:23.
2. Winter, G. & Milstein, C. 1991. Man-made antibodies. *Nature.* 349:293.
3. Vaughan, T. J., Osbourn, J. K., & Tempest, P. R. 1998. Human antibodies by design. *Nat. Biotechnol.* 16, 535.
4. Winter, G., Griffiths, A. D., Hawkins, R. E., & Hoogenboom, H. R. 1994. Making antibodies by phage display technology. *Annu. Rev. Immunol.* 12:433.
5. Burton, D. R., & Barbas, C. F. 1994. Human antibodies from combinatorial libraries. *Adv. Immunol.* 57:191.
6. Hoogenboom, H. R. 1997. Designing and optimizing library selection strategies for generating high-affinity antibodies. *Trends in Biotechnol.* 15:62.
7. Marks, J. D., Griffiths, A. D., Malmqvist, M., Clackson, T., Bye, J. M., & Winter, G. 1992. Bypassing immunisation: high affinity human antibodies by chain shuffling. *Bio/Technology.* 10:779.
8. Clackson, T., Hoogenboom, H. R., Griffiths, A. D., & Winter, G. 1991. Making antibody fragments using phage display libraries. *Nature.* 352:624.
9. Hawkins, R. E., Russel, S. J., & Winter. G. 1992. Selection of phage antibodies by binding affinity: mimicking affinity maturation. *J. Mol. Biol.* 226;889.
10. Low, N. M., Holliger, P. H., & Winter, G. 1996. Mimicking somatic hypermutation: affinity maturation of antibodies displayed on bacteriophage using a bacterial mutator strain. *J. Mol. Biol.* 260,359.
11. Barbas, C. F., Hu, D., Dunlop, N., Sawyer, L., Cababa, D., Hendry, R. M., Nara, P. L., & Burton, D. R. 1994. In vitro evolution of a neutralizing human antibody to human immunodeficiency virus type 1 to enhance affinity and broaden strain cross-reactivity. *Proc. Natl. Acad. Sci. USA.* 91:3809.
12. Yang, W.-P., Green, K., Pinz-Sweeney, S., Briones, A. T., Burton, D. R., & Barbas, C. F. 1995. CDR walking mutagenesis for the affinity maturation of a potent human ant-HIV-1 antibody into the picomolar range. *J. Mol. Biol.* 254:392.
13. Balint, R. F., & Larrick, J. W. 1993. Antibody engineering by parsimonious mutagenesis. *Gene.* 137:109.
14. Schier, R., Bye, J., Apell, G., McCall, A., Adams, G. P., Malmqvist, M., Weiner, L. M., & Marks, J. D. 1996. Isolation of high-affinity monomeric human anti-c-erbB-2 single chain Fv using affinity-driven selection. *J. Mol. Biol.* 255:28.
15. Chowdhury P S, Pastan I. 1999. Improving antibody affinity by mimicking somatic hypermutation in vitro. Nat Biotechnol 17:568.
16. Neri D, Carnemolla B, Nissim A, Leprini A, Querze G, Balza E, Pini A, Tarli L, Halin C, Neri P, Zardi L, Winter G. 1997. Targeting by affinity-matured recombinant antibody fragments of an angiogenesis associated fibronectin isoform. Nat Biotechnol 12:1271.
17. Huls, G. A., et al. 1999. A recombinant, fully human monoclonal antibody with antitumor activity constructed from phage-displayed antibody fragments. *Nature Biotechnology.* 17:276.
18. Stemmer, W. P. C. 1994. DNA shuffling by random fragmentation and reassembly: In vitro recombination for molecular evolution. Proc. Natl. Acad. Sci. USA. 91:10747. 19 Stemmer, W. P. C. 1994. Rapid evolution of a protein in vitro by DNA shuffling. *Nature.* 370:389.
20. Foote, J., & Winter, G. 1992. Antibody framework residues affecting the conformation of the hypervariable loops. *J. Mol. Biol.* 224:487.
21. Wedemayer, G. J., Patten, P. A., Wang, L. H., Schultz, P. G., & Stevens, R. C. 1997. Structural insights into the evolution of an antibody combining site. *Science* 276:1665.
22. Mian, I. S., Bradwell, A. R., & Olson, A. J. 1991. Structure, function and properties of antibody binding sites. *J. Mol. Biol.* 217:133.
23. Davies, D. R., Padlan, E. A., & Sheriff, S. 1990. Antigen-antibody interactions. *Annu. Rev. Biochem.* 59:439.
24. www.mrc-cpe.ac.uk/imt-doc/public/INTRO.html Tomlinson, I. M., Williams, S. C., Corbett, S. J., Cox, J. P. L., & Winter, G. V 1997. Base: the database of human antibody genes. MRC Centre for Protein Engineering, Cambridge, UK.
25. Al-Lazikani, B., Lesk, A. M., & Chothia, C. 1997. Standard conformations for the canonical structures of immunoglobulins. *J. Mol. Riol.* 273:927.
26. Surfus, J. E., Hank, J. A., Oosterwijk, E., Welt, S., Lindstrom, M. J., Albertini, M. R., Schiller, H. J. H., & Sondel, P. M. 1996. Anti-renal-cell carcinoma chimeric antibody G250 facilitates antibody-dependent cellular cytotoxicity with in vitro and in vivo interleukin-2-activated effectors. *J. Immunother.* 3:184.
27. Denkers, E. Y., Badger, C. C., Ledbetter, J. A., & Bernstein, I. D. 1985. Influence of antibody isotype on passive serotherapy of lymphoma. *J. Immunol.* 135:2183.
28. Kaminski, M. S., Kitamura, K., Maloney, D. G., Campbell, M. J., & Levy, R. 1986. Importance of antibody isotype in monoclonal anti-idiotype therapy of a murine B cell lymphoma: a study of hybridoma class switch variants. *J. Immunol.* 136:1123.
29. Ghetie, M. A., Podar, E. M., Ilgen, A., Gordon, B. E., Uhr, J. W., & Vitetta, E. S. 1997. Homodimerization of tumor-reactive monoclonal antibodies markedly increases their ability to induce growth arrest or apoptosis of tumor cells. *Proc. Natl. Acad. Sci. USA.* 94:7509.
30. Tutt, A. L., et al. 1998. Monoclonal antibody therapy of B cell lymphoma: signalling activity on tumor cells apears more important that recruitment of effectors. *J. Immunol.* 161:3176.
31. Osdol, W., Fujimori, K., & Weinstein, J. N. 1991. An analysis of monoclonal antibody distribution in microscopic tumour nodules: Consequences of a "Binding Site Barrier". *Cancer Res.* 51:4778.
32. Langmuir, V. K., Mendonca, H. L., & Woo, D. V. 1992. Comparisons between two monoclonal antibodies that bind to the same antigen but have differing affinities: uptake kinetics and 125I-antibody therapy efficacy in multicell spheroids *Cancer Res.* 52:4728.
33. Hawkins, R. E., Russel, S. J., Baier, M., & Winter, G. 1993. The contribution of contact and non-contact residues of antibody in the affinity of binding to antigen *J. Mol. Biol.* 234:958.
34. Tomlinson, I. M. T., Walter, G., Jones, P. T., Dear, P. H., Sonhammer, E. L-L., & Winter, G. 1996. The imprint of somatic hypermutation on the repertoire of human germline V genes. *J. Mol. Biol.* 256:813.
35. Fujimori, K., Covell, D. C., Fletcher, J. E., & Weinstein, J. N. 1989. Modeling analysis of the global and microscopic distribution of IgG, F(ab')$_2$ and Fab in tumors. *Cancer Res.* 49:5656.

36 Sung, C., Shockley, T. R., Morrison, P. F., Dvorak, H. F., Yarmush, M. L., & Dedrick, R. L. 1992. Predicted and observed effects of antibody affinity and antigen density on monoclonal antibody uptake in solid tumors. *Cancer Res.* 52: 377.

37 Van de Winkel, J. G. J., & Capel, P. J. A. 1993. Human IgG Fc receptor heterogeneity: molecular aspects and clinical implications. *Immunol. Today.* 14:215.

38 Van de Winkel, J. G. J., Boonen, G. J. J. C., Janssen, P. L. W., Vlug, A., Hogg, N., & Tax, W. J. M. 1989. Activity of two types of Fc receptors, FcγRI and FcγRII, in human monocyte cytotoxicity to sensitized erythrocytes. *Scand. J. Immunol.* 29:23.

39 Torigoe, C., Inman, J., & Metzger, H. 1998. An unusual mechanism for ligand antagonism. *Science.* 281:568.

40 McKeithan, T. W. 1995. Kinetic proofreading in T-cell receptor signal transduction. *Proc. Natl. Acad. Sci. USA* 92:5042.

41 Torigoe, C., Goldstein, B., Wofsy, C., & Metzger, H. 1997. Shuttling of initiating kinase between discrete aggregates of the high affinity receptor for IgE regulates the cellular response. *Proc. Natl. Acad. Sci. USA.* 94:1372.

42 Seya, T., Hara, T., Matsumoto, M., & Akedo, H. 1990. Quantitative analysis of membrane cofactor protein (MCP) of complement. J. Immunol. 145:238.

43 Panneerselvam, M., Welt, S., Old, L. J., & Vogel, C-W. 1986. A molecular mechanism of complement resistance of human melanoma cells. *J. Immunol.* 136:2534.

44 Cheung, N-K, V., Walter, E. I., Smith-Mensah, W. H., Ratnoff, W. D., Tykocinski, M. L., & Medof, M. E. 1988. Decay-accelerating factor protects human tumor cells from complement-mediated cytotoxicity in vitro. *J. Clin. Invest.* 81:1122.

45 Kumar, S., Vinci, J. M., Pytel, B. A., & Baglioni, C. 1993. Expression of messenger RNAs for complement inhibitors in human tissues and tumors. *Cancer Res.* 53:348.

46 Gorter, A., Block, V. T., Haasnoot, W. H. B., Ensink, N. G., Daha, M. R., & Fleuren, G. J. 1996. Expression of CD46, CD55, and CD59 on renal tumor cell lines and their role in preventing complement-mediated tumor cell lysis. *Lab. Invest.* 74:1039.

47 Berends, D., van der Kwast, T. H., de Both, N. J., & Mulder, P. G. 1989. Factors influencing antibody-mediated cytotoxicity during the immunotherapy of Rauscher-virus-induced myeloid leukemic cells. *Cancer Immunol. Immunother.* 28:123.

48 De Kruif, J., Boel, E., & Logtenberg, T. 1995. Selection and application of human single chain Fv antibody fragments from a semi-synthetic phage antibody display library with designed CDR3 regions. *J. Mol. Biol.* 248:97.

49 Boel, E. PhD. Thesis. 1998. University of Utrecht, The Netherlands.

50 Balzar, M., Bakker, H. A., Briaire-de-Bruijn, I. H., Fleuren, G. J., Warnaar, S. O., & Litvinov, S. V. 1998. Cytoplasmic tail regulates the intercellular adhesion function of the epithelial cell adhesion molecule. *Mol. Cell. Biol.* 18:4833.

51 Martin, A. C. R. & Thornton, J. M. 1996. Structural families in loops of homologous proteins: automatic classification, modelling and application of antibodies. *J. Mol. Biol.* 263:800.

52 Kwong, P. D., Wyatt, R., Robinson, J., Sweet, R. W., Sodroski, J., & Hendrickson, W. A. 1998. Structure of an HIV Gp120 envelope glycoprotein in complex with the CD4 receptor and a neutralizing human antibody. *Nature.* 393:648.

53 Sussman, J. L., et al. 1998. Database of Three-Dimensional Structure Information of Biological Macromolecules. *Acta Cryst.* D54:1078.

54 Pei, X. Y., Holliger, P., Murzin, A. G., & Williams, R. L. 1997. The 2.0-A resolution crystal structure of a trimeric antibody fragment with noncognate VH-VL domain pairs shows a rearrangement of VH CDR3. *Proc. Natl. Acad. Sci. USA.* 94:9637.

55 Willliams, G., et al. 1995. Dissection of the extracellular human interferon gamma receptor alpha-chain into two immunoglobulin-like domains. Production in an *Escherichia coli* thioredoxin gen fusion expression system and recognition by neutralizing antibodies. *Biochemistry* 34:1787.

56 Haynes, M. R., Stura, E. A., Hilvert, D., & Wilson, I. A. 1994. Routes to catalysis: structure of a catalytic antibody and comparison with its natural counterpart. *Science.* 263: 646.

57 Vriend, G. 1990. WHAT IF: A molecular modeling and drug design program. *J. Mol. Graph.* 8:52.

58 Laskowski, R. A., MacArthur, M. W., Moss, D. S., & Thornton, J. M. 1993. PROCHECK:A program to check the stereochemical quality of protein structures. *J. Appl. Cryst.* 265:283.

59 McDonald, I. K., & Thornton, J. M. 1994. Satisfying hydrogen bonding potential in proteins. *J. Mol. Biol.* 238: 577.

60 Wallace, A. C., Laskowski, R. A. & Thornton, J. M. 1995. LIGPLOT: A program to generate schematic diagrams of protein-ligand interactions. *Protein Eng.* 8:127.

61 Altschul, S. F., et al. 1997. Gapped BLAST and PSI-BLAST: a new generation of protein database search programs. *Nucleic Acids Res.* 25:3389.

62 Valerius, T., et al. 1993. Involvement of the high affinity receptor for IgG (FcγRI:CD64) in enhanced tumor cell cytotoxicity of neutrophils during G-CSF therapy. *Blood.* 82: 931.

63 Van Strijp, J. A. G., van Kessel, K. P. M., van der Tol, M. E., & Verhoef, J. 1989. Complement-mediated phagocytosis of herpes simplex virus by human granulocytes: binding or ingestion. *J. Clin. Invest.* 84:107.

64 Velders, M. P., van Rhijn, C. M., Oskam, E., Fleuren, G. J., Warnaar, S. O., & Litvinov, S. V. 1998. The impact of antigen density and antibody affinity on antibody-dependent cellular cytotoxicity: relevance for immunotherapy of carcinomas. *Br.J. Cancer.* 74:478.

65 Hjelstuen, M. H., Rasch-Halvorsen, K., Bruland, O., & De L Davies, C. 1998. Uptake, penetration, and binding of monoclonal antibodies with increasing affinity in human osteosarcoma multicell spheroids. *Anticancer Res.* 18:3153.

What is claimed is:

1. A molecule that binds to Ep-CAM, said molecule comprising a human heavy chain variable CDR3 region consisting of the amino acid sequence DPFLHY (SEQ ID NO: 6).

2. The molecule of claim 1, further comprising a human light chain variable CDR3 region, the CDR3 region consisting of the amino acid sequence MQALQTFTF (SEQ ID NO: 7).

3. The molecule of claim 1, characterized in that the molecule has an affinity constant for human Ep-CAM that is less than 5.0 nM.

4. The molecule of claim 1, characterized in that the molecule has an affinity constant for human Ep-CAM that is between 5.0 nM and 0.4 nM.

5. The molecule of claim 1, further comprising a human heavy chain variable CDR2 region, the CDR2 region consisting of the amino acid sequence IPIFGT (SEQ ID NO: 8) and a human heavy chain variable CDR1 region, the CDR1 region consisting of the amino acid sequence GGTFSSY (SEQ ID NO: 9).

6. The molecule of claim 1, wherein the molecule is an IgG1 molecule.

7. The molecule of claim 1, further comprising a fluorescent label.

8. The molecule of claim 1, further comprising a human heavy chain variable region consisting of the amino acid sequence of SEQ ID NO: 10.

9. The molecule of claim 1, further comprising a human light chain variable region consisting of the amino acid sequence of SEQ ID NO: 11.

10. A molecule that binds to Ep-CAM, comprising a human heavy chain variable region comprising a CDR3 region consisting of the amino acid sequence DPFLHY (SEQ ID NO: 6) and a human light chain variable region comprising a CDR1 region consisting of an amino acid sequence of RASQTISNNYLA (SEQ ID NO: 12) or RASOSVSSSYLA (SEQ ID NO: 13).

11. An antibody that binds to Ep-CAM, wherein the human heavy chain variable CDR3 region has an amino acid sequence consisting of SEQ ID NO: 6.

12. The antibody of claim 11, further comprising a human light chain variable CDR3 region having the amino acid sequence consisting of SEQ ID NO: 7.

13. The antibody of claim 11, characterized in that the antibody has an affinity constant for human Ep-CAM that is less than 5.0 nM.

14. The antibody of claim 11, characterized in that the antibody has an affinity constant for human Ep-CAM that is between 5.0 nM and 0.4 nM.

15. The antibody of claim 11, further comprising a human heavy chain variable CDR2 region having the amino acid sequence consisting of SEQ ID NO: 8 and a human heavy chain variable CDR1 region having the amino acid sequence consisting of SEQ ID NO: 9.

16. The antibody of claim 11, wherein the antibody is an IgG1.

17. The antibody of claim 11, further comprising a fluorescent label.

18. The antibody of claim 11, further comprising a human heavy chain variable region having the amino acid sequence consisting of SEQ ID NO: 10.

19. The antibody of claim 11, further comprising a human light chain variable region comprising a CDR1 region having an amino acid sequence consisting of SEQ ID NO: 12 or SEQ ID NO: 13.

20. The antibody of claim 11, further comprising a human light chain variable region having the amino acid sequence consisting of SEQ ID NO: 11.

* * * * *

UNITED STATES PATENT AND TRADEMARK OFFICE
CERTIFICATE OF CORRECTION

Page 1 of 2

PATENT NO. : 7,777,010 B2
APPLICATION NO. : 10/186186
DATED : August 17, 2010
INVENTOR(S) : Ton Logtenberg It is certified that error appears in the above-identified patent and that said Letters Patent is hereby corrected as shown below:

On the title page:
In ITEM (56) References Cited
U.S. PATENT DOCUMENTS
Page 1, 1st column, 4th line after last entry    insert title --FOREIGN PATENT DOCUMENTS-- below title
insert --EP    699 756    6/1996--

OTHER PUBLICATIONS
Page 1, 1st column, 1st line of the
   2nd entry (line 2),    change "J. Mol. Med. 91997)" to --J. Mol. Med. (1997)--

Page 1, 2nd column, 1st line of the
   5th entry (line 13),    change "byαβT Cell" to --by αβ T-Cell--
Page 2, 1st column, 2nd line of the
   4th entry (line 14),    change "a meutralizing" to --a neutralizing--

In the specification:
COLUMN 4,    LINE 15,    change "higher extend" to --higher extent--
COLUMN 5,    LINE 59,    change "UES-54" to --UBS-54--
COLUMN 7,    LINE 14,    change "member the" to --member of the--
COLUMN 7,    LINE 66,    change "UBS54" to --UBS-54--
COLUMN 8,    LINE 1,    change "2 * 107 individual" to --2 * $10^7$ individual--
COLUMN 10,    LINES 6-7,    change ""NACCES", Computer" to --"NACCESS," Computer--
COLUMN 10,    LINE 39,    change "95 viable" to --95% viable--
COLUMN 12,    LINE 6,    change "described (17)" to --described (17).--
COLUMN 12,    LINE 28,    change "told increase)." to --fold increase).--
COLUMN 13,    LINE 25,    change "in 10% lower" to --in ~10% lower--
COLUMN 13,    LINE 27,    change "UBS54" to --UBS-54--

Signed and Sealed this
Twentieth Day of September, 2011

David J. Kappos
*Director of the United States Patent and Trademark Office*

CERTIFICATE OF CORRECTION (continued)
U.S. Pat. No. 7,777,010 B2

In the specification:

| | |
|---|---|
| COLUMN 13, LINE 45, | change "UBS54" to --UBS-54-- |
| COLUMN 13, LINE 56, | change "dissociation rare" to --dissociation rate-- |
| COLUMN 14, LINE 42, | change "Position SerL$^{30}$" to --Position Ser$^{L30}$-- |
| COLUMN 15, LINE 41, | change "ant-HIV-1" to --anti-HIV-1-- |
| COLUMN 18, LINE 11, | change "2.0-A" to --2.0-Å-- |

In the claims:

CLAIM 10, COLUMN 34, LINE 2,     change "RASOSVSSSYLA" to --RASQSVSSSYLA--

SEQUENCE LISTING

<160> NUMBER OF SEQ ID NOS: 25

<210> SEQ ID NO 1
<211> LENGTH: 37
<212> TYPE: DNA
<213> ORGANISM: Artificial sequence
<220> FEATURE:
<223> OTHER INFORMATION: Primer Vkappa2-NCO-I

<400> SEQUENCE: 1
gcctccacct ccatgggata ttgtgatgac tcagtct                              37

<210> SEQ ID NO 2
<211> LENGTH: 43
<212> TYPE: DNA
<213> ORGANISM: Artificial sequence
<220> FEATURE:
<223> OTHER INFORMATION: Primer Vkappa2-XHO-I

<400> SEQUENCE: 2
gcctccacct ctcgagctgc tgacagtaat aagttgcaaa atc                       43

<210> SEQ ID NO 3
<211> LENGTH: 41
<212> TYPE: DNA
<213> ORGANISM: Artificial sequence
<220> FEATURE:
<223> OTHER INFORMATION: Primer NCO-I-VH1

<400> SEQUENCE: 3
gcctccacct ccatggccca ggtgcagctg gtgcagtctg g                         41

<210> SEQ ID NO 4
<211> LENGTH: 39
<212> TYPE: DNA
<213> ORGANISM: Artificial sequence
<220> FEATURE:
<223> OTHER INFORMATION: Primer VH XHO-I

<400> SEQUENCE: 4
gcctccacct ctcgagtctc gcacagtaat acacggccg                            39

<210> SEQ ID NO 5
<211> LENGTH: 87
<212> TYPE: DNA
<213> ORGANISM: Artificial sequence
<220> FEATURE:
<223> OTHER INFORMATION: spiked primer XHO-HCDR3-UBS-54
<220> FEATURE:
<221> NAME/KEY: misc_feature
<222> LOCATION: (43)..(45)
<223> OTHER INFORMATION: whereby "n" on positions 43, 44, and 45 stands
      for ATA, CAT, AGG or ACC
<220> FEATURE:
<221> NAME/KEY: misc_feature
<222> LOCATION: (46)..(51)
<223> OTHER INFORMATION: whereby "n" on positions  46, 47, and 48 stands
      for GTG, AAA, CTT or GGC; on 49, 50, and 51 "n" stands for AAG,
      CTA, AGT or ACC
<220> FEATURE:
<221> NAME/KEY: misc_feature
<222> LOCATION: (52)..(60)
<223> OTHER INFORMATION: whereby "n" on positions  52, 53 and 54 stands
      for AAA, CTT, AGG or ACC; on 55, 56 and 57 "n" stands for CGG,
      AAA, CTT or CCC; and on 58, 59 and 60 "n" stands for GTA, AAT,
      CGG or GCC

<400> SEQUENCE: 5

-continued

```
gcctccacct ctcgagacgg tgaccagggt accttggccc cannnnnnnn nnnnnnnnnn    60
tcttgcacag taatacacgg ccgtgtc                                        87
```

<210> SEQ ID NO 6
<211> LENGTH: 6
<212> TYPE: PRT
<213> ORGANISM: Artificial sequence
<220> FEATURE:
<223> OTHER INFORMATION: Heavy chain CDR3 region of UBS-54, A37 and C52

<400> SEQUENCE: 6

Asp Pro Phe Leu His Tyr
1               5

<210> SEQ ID NO 7
<211> LENGTH: 9
<212> TYPE: PRT
<213> ORGANISM: Artificial sequence
<220> FEATURE:
<223> OTHER INFORMATION: Light chain CDR3 region of UBS-54

<400> SEQUENCE: 7

Met Gln Ala Leu Gln Thr Phe Thr Phe
1               5

<210> SEQ ID NO 8
<211> LENGTH: 6
<212> TYPE: PRT
<213> ORGANISM: Artificial sequence
<220> FEATURE:
<223> OTHER INFORMATION: Heavy chain CDR2 region of UBS-54 and A37

<400> SEQUENCE: 8

Ile Pro Ile Phe Gly Thr
1               5

<210> SEQ ID NO 9
<211> LENGTH: 7
<212> TYPE: PRT
<213> ORGANISM: Artificial sequence
<220> FEATURE:
<223> OTHER INFORMATION: Heavy chain CDR1 region of UBS-54, A37 and C52

<400> SEQUENCE: 9

Gly Gly Thr Phe Ser Ser Tyr
1               5

<210> SEQ ID NO 10
<211> LENGTH: 112
<212> TYPE: PRT
<213> ORGANISM: Artificial sequence
<220> FEATURE:
<223> OTHER INFORMATION: Variable heavy chain of UBS-54 and A37

<400> SEQUENCE: 10

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Phe Leu His Tyr Trp Gly Gln Gly Thr Leu Val Thr
            100                 105                 110

<210> SEQ ID NO 11
<211> LENGTH: 110
<212> TYPE: PRT
<213> ORGANISM: Artificial sequence
<220> FEATURE:
<223> OTHER INFORMATION: Variable light chain of UBS-54

<400> SEQUENCE: 11

Glu Ile Glu Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Phe Thr Phe Gly Pro Gly Thr Lys Val Glu Ile
            100                 105                 110

<210> SEQ ID NO 12
<211> LENGTH: 12
<212> TYPE: PRT
<213> ORGANISM: Artificial sequence
<220> FEATURE:
<223> OTHER INFORMATION: Light chain CDR1 region of A37

<400> SEQUENCE: 12

Arg Ala Ser Gln Thr Ile Ser Asn Asn Tyr Leu Ala
 1               5                  10

<210> SEQ ID NO 13
<211> LENGTH: 12
<212> TYPE: PRT
<213> ORGANISM: Artificial sequence
<220> FEATURE:
<223> OTHER INFORMATION: Light chain CDR1 region of C52

<400> SEQUENCE: 13

Arg Ala Ser Gln Ser Val Ser Ser Ser Tyr Leu Ala
 1               5                  10

<210> SEQ ID NO 14
<211> LENGTH: 222
<212> TYPE: PRT
<213> ORGANISM: Artificial sequence
<220> FEATURE:
<223> OTHER INFORMATION: Amino acid sequence of UBS-54

<400> SEQUENCE: 14

Gln Val Gln Leu Val Gln Ser Gly Ala Glu Val Lys Lys Pro Gly Ser
 1               5                  10                  15
```

-continued

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Tyr Trp Gly Gln Gly Thr Leu Val Thr
            100                 105                 110

Glu Ile Glu Leu Thr Gln Ser Pro Leu Ser Leu Pro Val Thr Pro Gly
        115                 120                 125

Glu Pro Ala Ser Ile Ser Cys Arg Ser Ser Gln Ser Leu Leu His Ser
130                 135                 140

Asn Gly Tyr Asn Tyr Leu Asp Trp Tyr Leu Gln Lys Pro Gly Gln Ser
145                 150                 155                 160

Pro Gln Leu Leu Ile Tyr Leu Gly Ser Asn Arg Ala Ser Gly Val Pro
                165                 170                 175

Asp Arg Phe Ser Gly Ser Gly Ser Gly Thr Asp Phe Thr Leu Lys Ile
            180                 185                 190

Ser Arg Val Glu Ala Glu Asp Val Gly Val Tyr Tyr Cys Met Gln Ala
        195                 200                 205

Leu Gln Thr Phe Thr Phe Gly Pro Gly Thr Lys Val Glu Ile
210                 215                 220

<210> SEQ ID NO 15
<211> LENGTH: 219
<212> TYPE: PRT
<213> ORGANISM: Artificial sequence
<220> FEATURE:
<223> OTHER INFORMATION: Amino acid sequence of A37

<400> SEQUENCE: 15

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Tyr Trp Gly Gln Gly Thr Leu Val Thr
            100                 105                 110

Glu Ile Glu Leu Thr Gln Ser Pro Gly Thr Leu Ser Leu Ser Pro Gly
        115                 120                 125

Glu Arg Ala Thr Leu Ser Cys Arg Ala Ser Gln Thr Ile Ser Asn Asn
130                 135                 140

Tyr Leu Ala Trp Tyr Gln Gln Lys Arg Gly Gln Ala Pro Arg Leu Leu
145                 150                 155                 160

Ile Tyr Ala Ala Ser Ser Arg Ala Thr Gly Ile Pro Asp Arg Phe Ser
            165                 170                 175

Gly Thr Gly Ser Gly Thr Asp Phe Thr Leu Thr Ile Ser Arg Leu Glu
            180                 185                 190

Pro Glu Asp Phe Ala Val Tyr Tyr Cys Ala Gln Gly Glu Leu Tyr Pro
            195                 200                 205

Arg Gln Phe Gly Gly Gly Thr Lys Leu Glu Ile
    210                 215

<210> SEQ ID NO 16
<211> LENGTH: 219
<212> TYPE: PRT
<213> ORGANISM: Artificial sequence
<220> FEATURE:
<223> OTHER INFORMATION: Amino acid sequence of C52

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Val Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Tyr Trp Gly Gln Gly Thr Leu Val Thr
            100                 105                 110

Glu Ile Glu Leu Thr Gln Ser Pro Gly Thr Leu Ser Leu Ser Pro Gly
        115                 120                 125

Glu Arg Ala Thr Leu Ser Cys Arg Ala Ser Gln Ser Val Ser Ser Ser
    130                 135                 140

Tyr Leu Ala Trp Tyr Gln Gln Lys Pro Gly Gln Ala Pro Arg Leu Leu
145                 150                 155                 160

Ile Tyr Gly Ala Ser Ser Arg Ala Thr Gly Ile Pro Asp Arg Phe Ser
            165                 170                 175

Gly Ser Gly Ser Gly Thr Asp Phe Thr Leu Thr Ile Ser Arg Leu Glu
            180                 185                 190

Pro Glu Asp Phe Ala Val Tyr Tyr Cys Ala Gln Gly Glu Leu Tyr Pro
            195                 200                 205

Arg Gln Phe Gly Gly Gly Thr Lys Leu Asp Ile
    210                 215

<210> SEQ ID NO 17
<211> LENGTH: 16
<212> TYPE: PRT
<213> ORGANISM: Artificial sequence
<220> FEATURE:
<223> OTHER INFORMATION: Light chain CDR1 region of UBS-54

<400> SEQUENCE: 17

Arg Ser Ser Gln Ser Leu Leu His Ser Asn Gly Tyr Asn Tyr Leu Asp
1               5                   10                  15

<210> SEQ ID NO 18

```
<210> SEQ ID NO 18
<211> LENGTH: 7
<212> TYPE: PRT
<213> ORGANISM: Artificial sequence
<220> FEATURE:
<223> OTHER INFORMATION: Light chain CDR2 region of UBS-54

<400> SEQUENCE: 18

Leu Gly Ser Asn Arg Ala Ser
1               5

<210> SEQ ID NO 19
<211> LENGTH: 7
<212> TYPE: PRT
<213> ORGANISM: Artificial sequence
<220> FEATURE:
<223> OTHER INFORMATION: Light chain CDR2 region of A37

<400> SEQUENCE: 19

Ala Ala Ser Ser Arg Ala Thr
1               5

<210> SEQ ID NO 20
<211> LENGTH: 10
<212> TYPE: PRT
<213> ORGANISM: Artificial sequence
<220> FEATURE:
<223> OTHER INFORMATION: Light chain CDR3 region of A37 and C52

<400> SEQUENCE: 20

Ala Gln Gly Glu Leu Tyr Pro Arg Gln Phe
1               5                   10

<210> SEQ ID NO 21
<211> LENGTH: 6
<212> TYPE: PRT
<213> ORGANISM: Artificial sequence
<220> FEATURE:
<223> OTHER INFORMATION: Heavy chain CDR2 region of C52

<400> SEQUENCE: 21

Val Pro Ile Phe Gly Thr
1               5

<210> SEQ ID NO 22
<211> LENGTH: 7
<212> TYPE: PRT
<213> ORGANISM: Artificial sequence
<220> FEATURE:
<223> OTHER INFORMATION: Light chain CDR2 region of C52

<400> SEQUENCE: 22

Gly Ala Ser Ser Arg Ala Thr
1               5

<210> SEQ ID NO 23
<211> LENGTH: 107
<212> TYPE: PRT
<213> ORGANISM: Artificial sequence
<220> FEATURE:
<223> OTHER INFORMATION: Variable light chain of A37

<400> SEQUENCE: 23

Glu Ile Glu Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Asn Asn
            20                  25                  30
```

```
Tyr Leu Ala Trp Tyr Gln Gln Lys Arg Gly Gln Ala Pro Arg Leu Leu
            35                  40                  45

Ile Tyr Ala Ala Ser Arg Ala Thr Gly Ile Pro Asp Arg Phe Ser
     50                  55                  60

Gly Thr Gly Ser Gly Thr Asp Phe Thr Leu Thr Ile Ser Arg Leu Glu
65                   70                  75                  80

Pro Glu Asp Phe Ala Val Tyr Tyr Cys Ala Gln Gly Glu Leu Tyr Pro
                 85                  90                  95

Arg Gln Phe Gly Gly Gly Thr Lys Leu Glu Ile
            100                 105
```

<210> SEQ ID NO 24
<211> LENGTH: 112
<212> TYPE: PRT
<213> ORGANISM: Artificial sequence
<220> FEATURE:
<223> OTHER INFORMATION: Variable heavy chain of C52

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Val Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Asp Pro Phe Leu His Tyr Trp Gly Gln Gly Thr Leu Val Thr
            100                 105                 110
```

<210> SEQ ID NO 25
<211> LENGTH: 107
<212> TYPE: PRT
<213> ORGANISM: Artificial sequence
<220> FEATURE:
<223> OTHER INFORMATION: Variable light chain of C52

<400> SEQUENCE: 25

```
Glu Ile Glu Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
65                   70                  75                  80

Pro Glu Asp Phe Ala Val Tyr Tyr Cys Ala Gln Gly Glu Leu Tyr Pro
                 85                  90                  95

Arg Gln Phe Gly Gly Gly Thr Lys Leu Asp Ile
            100                 105
```